United States Patent [19]

Capozzi et al.

[11] Patent Number: 4,978,336
[45] Date of Patent: Dec. 18, 1990

[54] BIOLOGICAL SYRINGE SYSTEM

[75] Inventors: Emil E. Capozzi, Costa Mesa; H. Stephen Cookston, Pacific Palisades, both of Calif.

[73] Assignee: Hemaedics, Inc., Malibu, Calif.

[21] Appl. No.: 418,707

[22] Filed: Oct. 3, 1989

Related U.S. Application Data

[63] Continuation of Ser. No. 102,543, Sep. 29, 1987, abandoned.

[51] Int. Cl.$^5$ .............................................. A61M 37/00
[52] U.S. Cl. ..................................... 604/82; 604/191; 222/137; 239/398; 239/432
[58] Field of Search ................... 604/94, 191, 283, 82, 604/85, 905, 240, 242, 243; 239/398, 432; 600/4, 5; 222/137, 129, 145

[56] References Cited

U.S. PATENT DOCUMENTS

| | | | |
|---|---|---|---|
| 2,158,593 | 5/1939 | Scrimgeour | 604/242 |
| 3,179,107 | 4/1965 | Clark | 604/242 |
| 4,040,420 | 8/1977 | Speer | 604/272 X |
| 4,109,653 | 8/1978 | Kozam | 604/191 |
| 4,359,049 | 11/1982 | Redl et al. | 604/191 |
| 4,629,455 | 12/1986 | Kanno | 604/905 |
| 4,631,055 | 12/1986 | Redl et al. | 604/191 |
| 4,735,616 | 4/1988 | Eibl et al. | 604/191 |
| 4,743,229 | 5/1988 | Chu | 604/82 |
| 4,842,581 | 6/1989 | Davis | 604/38 |
| 4,874,368 | 10/1989 | Miller et al. | 604/82 |

Primary Examiner—C. Fred Rosenbaum
Assistant Examiner—Mark O. Polutta
Attorney, Agent, or Firm—Beehler & Pavitt

[57] ABSTRACT

Syringe holder carriers first and second syringes which contain proteins which, when mixed, become a tissue adhesive. A manifold locks onto the two syringes, receives the two streams and delivers them to an output nose. A standard needle detachably locks onto the nose of the manifold. Alternatively to a needle, a spray nozzle can be locked thereon.

4 Claims, 2 Drawing Sheets

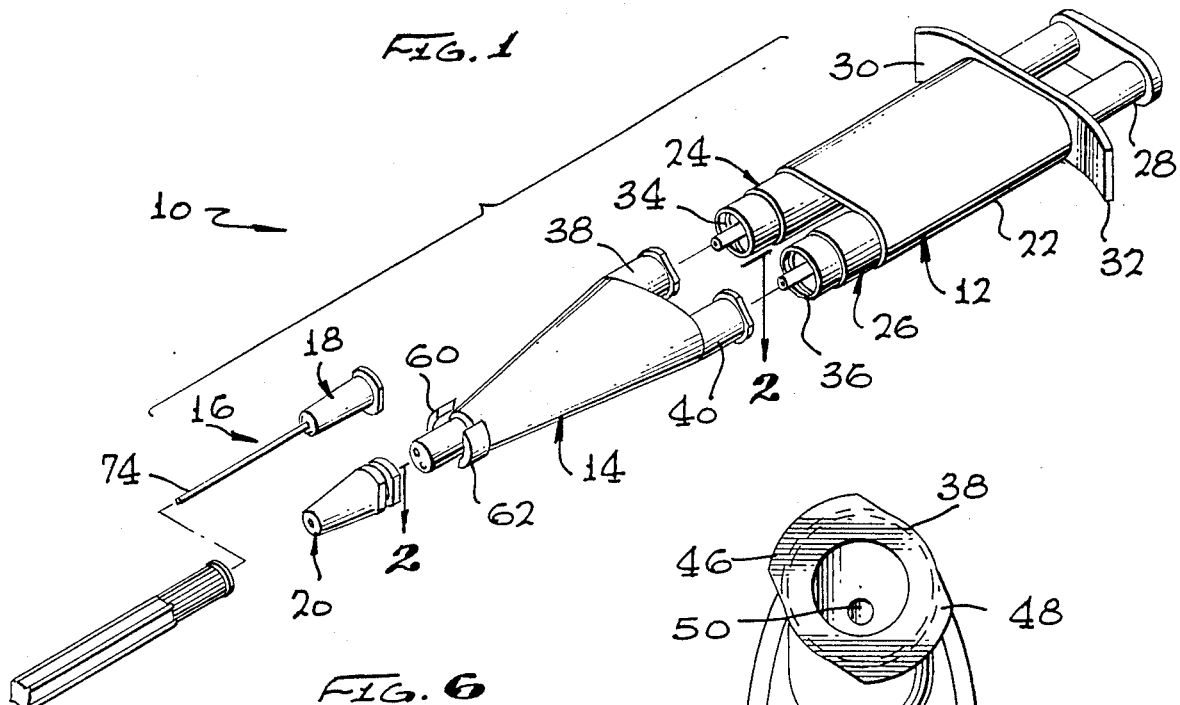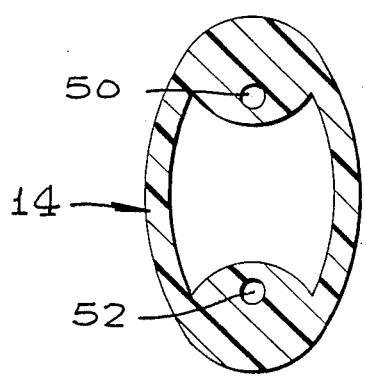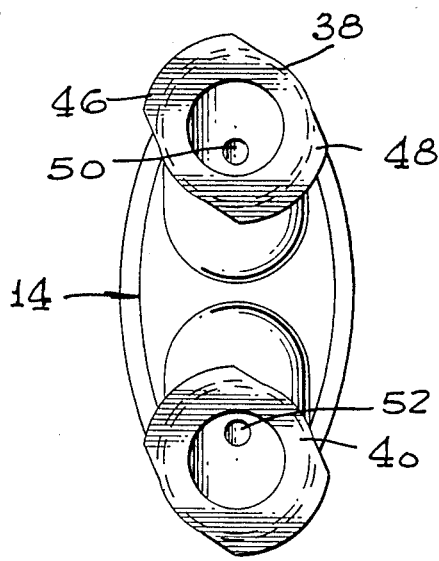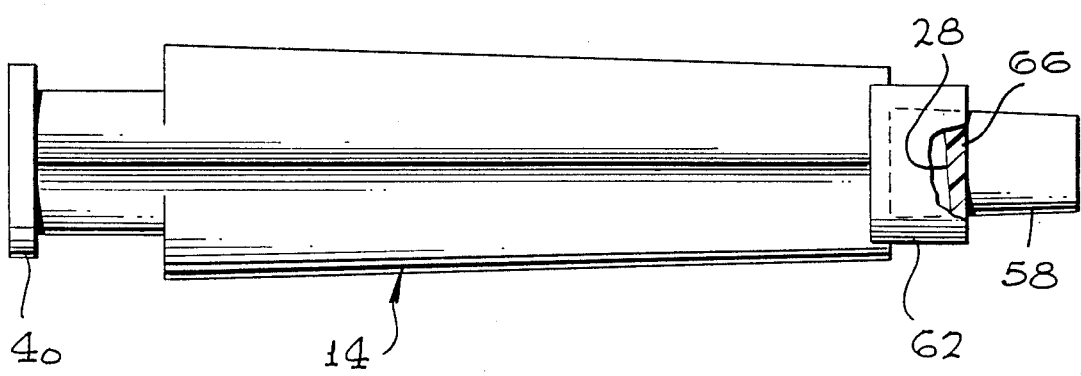

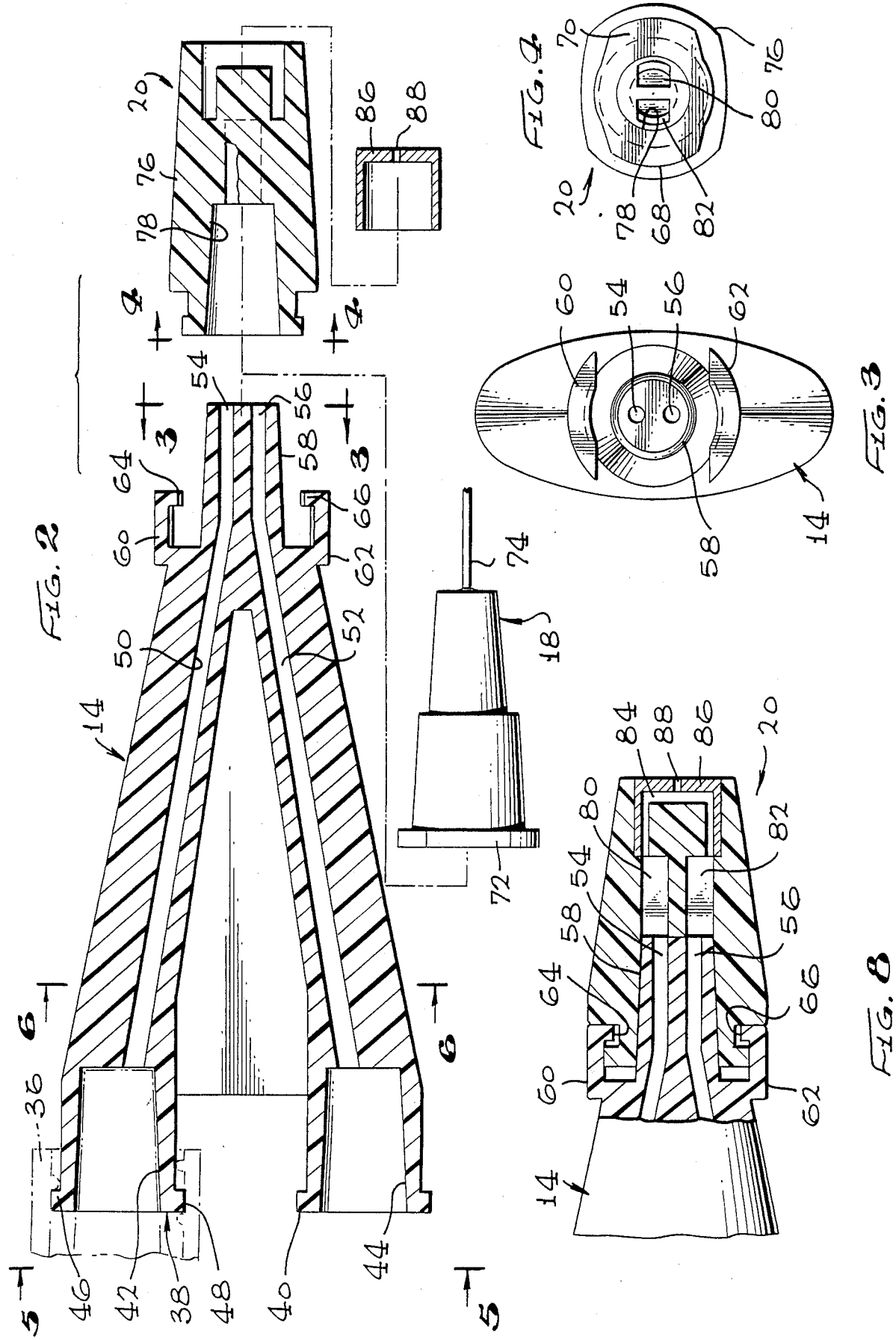

BIOLOGICAL SYRINGE SYSTEM

This is a continuation of co-pending application Ser. No. 07/102,543 filed on Sept. 29, 1987, now abandoned.

FIELD OF THE INVENTION

This invention is directed to a biological syringe system wherein two syringes separately deliver proteins which form a tissue adhesive, and wherein a manifold locks onto the syringes and a needle locks onto the manifold to deliver the mixed proteins to promote coagulation and healing.

BACKGROUND OF THE INVENTION

A biological tissue adhesive is formed when a water solution containing blood factor XIII and fibrinogen is mixed with a water solution containing thrombin. The rate at which the adhesive sets or hardens principally depends upon the thrombin concentration. The mixture is applied to the laceration site which is to be adhered or protected. Previous methods of application included applying one solution to the site of adhesion and then applying the other solution thereto. The disadvantage of this method is that inadequate mixing occurs at the site to result in setting of the adhesive at the interface between the two solutions, without good adhesion to the adjacent biological surfaces.

Another method of application comprises the premixing of the two solutions in a mixing vessel, whereupon it is drawn into a syringe and then applied to the site to be adhered. This method requires promptness of application since the setting of the adhesive starts when the two solutions are combined. The time from mixing to the time of application to the site must be quite short, and depends upon the concentration of the thrombin solution.

In another method of application, two syringes are clamped together and the output cones are inserted into a Y-piece. When the mixing occurs in the Y-piece, the adhesive setting also occurs therein to plug it up. When the mixing occurs in the needle connected onto the Y-piece, plug-up of the needle causes buildup of pressure in the Y-piece so that the needle may be separated and injected into the field, possibly into the patient. Thus, there is need for a biological syringe system wherein the needle and other parts cannot become inadvertently detached so that no parts are ejected.

SUMMARY OF THE INVENTION

In order to aid in the understanding of this invention, it can be stated in essentially summary form that it is directed to a biological syringe system wherein a manifold is configured to detachably lock to a pair of syringes and is also configured to detachably lock to a hollow needle so that two fluids can be delivered by two syringes for delivery by one hollow needle.

It is, thus, an object and advantage of this invention to provide a biological syringe system wherein two syringes are detachably locked to a manifold so that they can be secured in a manner with respect thereto that they cannot become inadvertently separated, and a single needle can be detachably locked to the manifold to receive the two fluid streams from the two syringes and deliver them in one needle.

It is another purpose and advantage of this invention to provide a biological syringe system wherein the parts are detachably locked together and cannot be inadvertently separated.

It is another object and advantage of this invention to provide a biological syringe system which is inexpensive so that it can be employed to deliver a tissue adhesive to tissue which requires attachment, covering or sealing and can be discarded after use to obviate the need for cleaning up the set tissue adhesive.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is an exploded perspective view of the biological syringe system of this invention.

FIG. 2 is an enlarged section through the manifold thereof, as seen generally along the line 2—2 of FIG. 1.

FIG. 3 is an end view of the manifold, as seen generally along the line 3—3 of FIG. 2.

FIG. 4 is an end view of an adhesive spray fitting, as seen generally along the line 4—4 of FIG. 2.

FIG. 5 is an end view of the manifold, as seen generally along the line 5—5 of FIG. 2.

FIG. 6 is a section through the manifold, as seen generally along the line 6—6 of FIG. 2.

FIG. 7 is an edge view of the manifold, with parts broken away and parts taken in section FIG. 8 is an enlarged section through the adhesive spray fitting, shown in exploded position in FIG. 2.

DESCRIPTION OF THE PREFERRED EMBODIMENT

The biological syringe system of this invention is generally indicated at 10 in FIG. 1. The syringe system comprises a syringe holder 12, manifold 14 and adhesive applicator 16. The adhesive applicator 16 is generally indicated in FIG. 1 because it may be either a needle assembly 18 or a spray assembly 20. The manifold 14 is shown in more detail in FIGS. 2, 5, 6 and 7. The needle assembly is shown in more detail in FIG. 2, and the spray assembly is shown in more detail in FIGS. 2, 4 and 8.

The syringe holder 12, as seen in FIG. 1, has a channel-shaped body 22 which is open on the bottom, as seen in FIG. 1, to detachably receive two syringes 24 and 26. Cap 28 engages the plungers of both syringes so that the plungers are depressed at the same time and speed. Flanges 30 and 32 permit one-handed grasp of the syringe holder, in the fingers so that the user's thumb can depress the syringe plungers together. Syringes 24 and 26 are respectively fitted at their forward ends with lock fittings 34 and 36. These lock fittings are suitable to detachably lock together with companion fittings on manifold 14. Lock fitting 36 is shown in dashed lines in FIG. 2.

Manifold 14 is configured to detachably lock to the syringes and bring the output streams thereof close together. Manifold 14 is in the form of a conical ellipsoid which has lock fittings 38 and 40 at its right end. These lock fittings respectively have conical seal joints 42 and 44 thereon to receive the conical nose on their respective syringes and seal with respect thereto. Lock fittings 38 and 40, see FIG. 5, each have a pair of ears extending from the otherwise generally cylindrical exterior surface. Ears 46 and 48 are shown with respect to fitting 38. The nose of the syringe has exterior of its conical nose a cylindrical sleeve which extends over the ears 46 and 48 and has inclined flanges which engage under the ears 46 and 48 so that when inserted, a quarter turn locks the fitting together. The structure of the nose of the syringe will be described in more detail with respect to the small end of the manifold.

Component channels 50 and 52 extend separately through the manifold from the conical recesses 42 and 44 which receive the noses of the syringes to the right end of the manifold, as seen in FIG. 2. At the right end, they form separate exit channels 54 and 56 in the truncated conical forward nose 58 of the manifold. The conical nose is the same size as the conical cone on each syringe. A collar surrounds the conical nose, but the collar is interrupted to form collar segments 60 and 62, particularly see FIG. 3. The respective collar segments 60 and 62 carry flanges 64 and 66 which have an angular inner surface in the axial direction towards the larger end of the cone. The collar segments and flanges are sized so that the ears 68 and 70 on spray assembly 20, see FIG. 4, and the corresponding ears on needle 18, with ear 72 shown in FIG. 2, fit between the collar segment when ears are correctly oriented and lock behind the collar segments when the spray assembly or needle assembly is rotated a quarter turn in the clockwise direction, as looking axially towards the larger end of the conical nose.

Needle assembly 18 is configured to receive the conical nose 58 and have its ears, including ear 72, pass between the flanges 64 and 66, and upon rotation, the ears lock behind the flanges to hold the needle assembly in place. The needle assembly has a large enough interior passage to receive outflow from both exit channels 54 and 56, and this outflow passes through needle 74 and is mixed therein so that at the needle tip, mixed adhesive is delivered. FIG. 7 shows the collar segment 62 broken away to expose flange 66 and show its angular locking surface 78.

Rather than delivering the mixed adhesive by needle, sometimes it is desirable to spray the mixed adhesive on a surface. This is achieved by spray assembly 20 which has a body 76. The body 76 has a conical interior surface 78, seen in FIG. 2, which meets and seals with the conical nose 58, as shown in FIG. 8. As seen in FIG. 4, ears 68 and 70 are formed on the body and are sized to pass between the collar segments 60 and 62, as previously described, and upon rotation of the body 76 locked behind the flanges 64 and 66. Spray assembly body 76 has separate passages 80 and 82 which respectively align with channels 54 and 56 when the spray assembly body is locked in place, as shown in FIG. 8. The locking structure aligns the passages with the channel to assure passage continuity. The passages 80 and 82 open into space 84 where the fluids are mixed. The space 84 is covered by spray nozzle 86 which has a spray outlet 88. The mixed fluid sprays out of outlet 88 to be applied to the selected surface.

It is critical that the needle assembly or the spray assembly, whichever is selected, be detachably locked to the manifold. It must be detachable so that it may be changed, and locked on so that it cannot become inadvertently driven off. For example, after one use of the biological syringe system with the needle assembly in place, the mixed fluid remains within the needle 74. If the system is returned to use before the tissue adhesive sets up within the needle, it can be reused, but if the adhesive sets up in the needle, the needle must be changed. In the interim condition, if the user attempts to use it and builds up pressure against the plugged-up or almost plugged-up needle, the needle assembly can be ejected. Such is undesirable. Therefore, the needle locking system onto the manifold is critical. It is also critical to lock the spray assembly in place, and it is selected because the biological adhesive also mixes within the spray assembly. Ejection of the spray assembly is not as dangerous, but a loose piece in an operating field is to be avoided.

The locking of the manifold onto the syringes maintains the conical seal so that the biological fluid cannot escape. In the previous condition of plug-up of the needle assembly or spray assembly, actuation of the syringe plungers builds up pressure and could drive the manifold, at least loose and possibly separate from the syringes. When loose, biological fluid escapes, to the detriment of the field, and if the manifold comes loose, it is also a detriment to the field.

This invention has been disclosed in its most preferred embodiment, and it is clear that it is susceptible to numerous modifications and embodiments within the ability of those skilled in the art and without the exercise of the inventive faculty. Accordingly, the scope of this invention is defined by the scope of the following claims.

What is claimed is:

1. A biological syringe system for delivering a first and second fluid in a mixed composition said biological syringe system including a first and second syringe for holding said first and second fluids, and a corresponding first and second plunger for forcing said first and second fluids from said first and second syringes respectively, comprising:

a manifold, said manifold having first and second corresponding component channels therethrough, and first and second input connections respectively communicating with said first and second component channels, said first and second component channels terminating in corresponding exit channels adjacent to each other on an opposing end of said manifold;

a discharge assembly coupled to said opposing end of said manifold and receiving fluid from both of said exit channels, said discharge assembly for mixing fluid from both of said exit channels and delivering said mixed fluid in a spray, said discharge assembly having a first and second passage therethrough communicating with said exit channels from said manifold for carrying fluid from said first and second component channels in corresponding first and second passages within said discharge assembly while maintaining said first and second fluids separated from each other, said discharge assembly having a mixing space defined therein to receive separate flows from said passages, said discharge assembly further comprising mixing means disposed within said mixing space to thoroughly mix said first and second fluids for the first time within said mixing space and to immediately thereafter atomize said thoroughly mixed first and second fluids in a spray discharged from said discharge assembly.

2. The biological syringe system of claim 1 wherein said means for thoroughly mixing and atomizing said first and second fluid into a spray comprises a shaped spray nozzle having a spray outlet defined therein, said shaped spray nozzle being disposed within said mixing space.

3. The biological syringe system of claim 2 wherein said first and second passages have outlet ends, and wherein said discharge assembly comprises a solid cylindrical body disposed within said mixing space, said solid cylindrical body having a first end surface adjacent outlet ends of said first and second passage in said discharge assembly, said first and second fluids exiting said outlet ends of said passages and flowing into a cylindrical annular space between said nozzle disposed in said mixing space and said cylindrical body disposed in said mixing space, said first and second fluids mixing for the first time within said cylindrical annular space and flowing to a portion of said mixing space adjacent an opposing end of said solid cylindrical body opposite said spray outlet, said mixed first and second fluids then being expressed through said spray outlet as atomized spray particles.

4. A method for applying a tissue adhesive and protective covering which chemically forms and hardens as applied comprising the steps of:

providing a first fluid;

providing a second fluid which when mixed with said first fluid hardens into said tissue adhesive;

forcing said first and second fluids from a corresponding first and second syringe into corresponding first and second passages;

partially mixing said first and second fluids together by flowing said fluids under pressure within a cylindrical annular space; and forcing said partially mixed first and second fluids from said cylindrical annular space into a final mixing chamber;

thoroughly mixing said first and second fluids in said final mixing chamber;

forcing said thoroughly mixed fluids to an axial spray orifice;

atomizing said thoroughly mixed first and second fluids by pressured ejection of said fluids through said spray orifice at a predetermined minimum pressure, whereby mixture of said first and second fluids is substantially improved, strength and hardening of said tissue adhesive substantially improved, and wherein thorough mixing occurs just prior to application in atomized form.

* * * * *